US011485957B2

(12) United States Patent
Niazi et al.

(10) Patent No.: US 11,485,957 B2
(45) Date of Patent: Nov. 1, 2022

(54) MODIFIED EC7 CELLS HAVING LOW TOXICITY TO VIRAL PRODUCTION PAYLOADS

(71) Applicant: NantBio, Inc., Culver City, CA (US)

(72) Inventors: Kayvan Niazi, Culver City, CA (US); Wael Tadros, Culver City, CA (US); Annie Shin, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 0 days.

(21) Appl. No.: 16/754,659

(22) PCT Filed: Oct. 9, 2018

(86) PCT No.: PCT/US2018/054982
§ 371 (c)(1),
(2) Date: Apr. 8, 2020

(87) PCT Pub. No.: WO2019/074907
PCT Pub. Date: Apr. 18, 2019

(65) Prior Publication Data
US 2020/0354687 A1    Nov. 12, 2020

Related U.S. Application Data

(60) Provisional application No. 62/633,412, filed on Feb. 21, 2018, provisional application No. 62/570,508, filed on Oct. 10, 2017.

(51) Int. Cl.
| | |
|---|---|
| *C12N 7/00* | (2006.01) |
| *C12N 15/861* | (2006.01) |
| *C12N 15/113* | (2010.01) |
| *C12N 15/62* | (2006.01) |
| *C12N 15/86* | (2006.01) |

(52) U.S. Cl.
CPC ............. *C12N 7/00* (2013.01); *C12N 15/113* (2013.01); *C12N 15/86* (2013.01); *C12N 2310/14* (2013.01); *C12N 2310/531* (2013.01); *C12N 2710/10343* (2013.01); *C12N 2710/10352* (2013.01)

(58) Field of Classification Search
None
See application file for complete search history.

(56) References Cited

U.S. PATENT DOCUMENTS

| | | | |
|---|---|---|---|
| 6,025,192 A | 2/2000 | Beach et al. | |
| 6,548,286 B1 | 4/2003 | Samulski et al. | |
| 8,138,327 B2 | 3/2012 | Unwalla et al. | |
| 8,273,722 B2 | 9/2012 | Ladine et al. | |
| 2002/0045250 A1* | 4/2002 | Wadsworth | C12N 15/86 435/320.1 |
| 2004/0043490 A1 | 3/2004 | Shimada | |
| 2010/0173359 A1 | 7/2010 | LaDine et al. | |
| 2013/0217121 A1 | 8/2013 | Spayd et al. | |
| 2015/0252080 A1 | 9/2015 | Stone et al. | |
| 2016/0333373 A1 | 11/2016 | Farley et al. | |
| 2017/0029785 A1 | 2/2017 | Zhao et al. | |
| 2017/0100479 A1 | 4/2017 | Wu et al. | |
| 2018/0305439 A1* | 10/2018 | Kafri | C07K 14/745 |

FOREIGN PATENT DOCUMENTS

| | | | | |
|---|---|---|---|---|
| CA | 3 077 594 A1 | 4/2019 | | |
| CN | 101787373 A | 7/2010 | | |
| EP | 0 566 732 B1 | 4/2003 | | |
| JP | 2002-153278 A | 5/2002 | | |
| JP | 2008-545406 A | 12/2008 | | |
| JP | 2013-515731 A | 5/2013 | | |
| JP | 2020-519294 A | 7/2020 | | |
| KR | 10-2020-0055141 A | 5/2020 | | |
| TW | 201923074 A | 6/2019 | | |
| WO | 91/13979 A1 | 9/1991 | | |
| WO | 9846728 A1 | 10/1998 | | |
| WO | WO 2000/06751 A2 * | 2/2000 | ............. | C12N 15/72 |
| WO | 2005/063984 A1 | 7/2005 | | |
| WO | 2007/000668 A2 | 1/2007 | | |
| WO | 2011/079077 A1 | 6/2011 | | |
| WO | 2015/114365 A1 | 8/2015 | | |
| WO | 2017100338 A1 | 6/2017 | | |
| WO | 2018/209216 A1 | 11/2018 | | |
| WO | 2019074907 A1 | 4/2019 | | |

OTHER PUBLICATIONS

Lai et al, Comparison between the Repression Potency of siRNA Targeting the Coding Region and the 3◆◆-Untranslated Region of mRNA, BioMed Research International, 2013, pp. 1-5.*
Pear et al, Production of high-titer helper-free retroviruses by transient transfection, Proc. Natl. Acad. Sci. USA vol. 90, pp. 8392-8396, Sep. 1993.*
Vicenti et al, Comparative analysis of different cell systems for Zika virus (ZIKV) propagation and evaluation of anti-ZIKV compounds in vitro, Virus Research vol. 244, Jan. 15, 2018, pp. 64-70.*
Albrecht et al, Comparison of Lentiviral Packaging Mixes and Producer Cell lines for RNAi Applications, Mol Biotechnol (2015) 57: 499-505.*
Wei N, Zhang L, Huang H, Chen Y, Zheng J, et al. (2012) siRNA Has Greatly Elevated Mismatch Tolerance at 39-UTR Sites. PLoS ONE 7(11): e49309, pp. 1-9.*
Strobel et al, Riboswitch-mediated Attenuation of Transgene Cytotoxicity Increases Adeno-associated Virus Vector Yields in HEK-293 Cells, Molecular Therapy, 2015, pp. 1582-1591.*

(Continued)

*Primary Examiner* — Maria Marvich
(74) *Attorney, Agent, or Firm* — Martin Fessenmaier; Umberg Zipser LLP

(57) ABSTRACT

Recombinant cells and methods therefor are contemplated that allow for rapid and high titer production of recombinant viruses, and especially replication deficient Ad5 virus. In some preferred aspects, the host cell is modified to produce an inhibitor that reduces or eliminates the expression of a therapeutic protein encoded in the virus, while in other aspects, the virus includes a gene that directly or indirectly reduces or eliminates the expression of a therapeutic protein encoded in the virus. Most preferably, shRNA encoded by the host cell will reduce or suppress expression of a payload gene encoded in the recombinant virus.

8 Claims, 15 Drawing Sheets

Specification includes a Sequence Listing.

(56) References Cited

OTHER PUBLICATIONS

Xia et al, Multiple shRNAs expressed by an inducible pol II promoter can knockdown the expression of multiple target genes, BioTechniques 41:64-68 (Jul. 2006).*

Wang et al An shRNA Silencing a Non-Toxic Transgene Reduces Nutrient Consumption and Increases Production of J. Cell. Physiol. 219: 365-371, 2009.*

Yu et al, Lentiviral Vectors with Two Independent Internal Promoters Transfer High-Level Expression of MultipleTransgenes to Human Hematopoietic Stem-Progenitor Cells, Molecular Therapy, 2003, pp. 827-838.*

Zhang et al, Identification of Human Butyrylcholinesterase Organophosphate-Resistant Variants through a Novel Mammalian Enzyme Functional Screen, The Journal of Pharmacology and Experimental Therapeutics, 2012, pp. 673-682.*

Gall et al, Rescue and Production of Vaccine and Therapeutic Adenovirus Vectors Expressing Inhibitory Transgenes, Molecular Biotechnology, 2007, pp. 263-273.*

Bergelson et al., "Isolation of a common receptor for Coxsackie B viruses and adenoviruses 2 and 5", Science, Feb. 28, 1997, vol. 275, pp. 1320-1323 (Cited from Specification).

Walters et al., "Basolateral Localization of Fiber Receptors Limits Adenovirus Infection from the Apical Surface of Airway Epithelia", The Journal of Biological Chemistry, 1999, vol. 274, No. 15, pp. 10219-10226 (Cited from Specification).

Amalfitano et al., "Production and characterization of improved adenovirus vectors with the E1, E2b, and E3 genes deleted", Journal of Virology, Feb. 1998, vol. 72, No. 2, pp. 926-933 (Cited from Specification).

Thaisuchat et al., "Identification of a novel temperature sensitive promoter in cho cells", BMC Biotechnology, 2011, vol. 11, No. 51, pp. 1-12 (Cited from Specification).

Lee et al., "A novel chimeric promoter that is highly responsive to hypoxia and metals", Gene Therapy, 2006, vol. 13, pp. 857-868 (Cited from Specification).

Gupta et al., "Latent Membrane Protein 1 as a molecular adjuvant for single-cycle lentiviral vaccines", Retrovirology, 2011, vol. 8, No. 39, pp. 1-12.

Maunder et al., "Enhancing titres of therapeutic viral vectors using the transgene repression in vector production (TRiP) system", Nature Communications, 2017, vol. 8, No. 14834, pp. 1-13.

Gupta et al., "Constitutively Active MAVS Inhibits HIV-1 Replication via Type I Interferon Secretion and Induction of HIV-1 Restriction Factors", Plos One, 2016, vol. 11, No. 2, pp. 1-25.

Wedler et al., "A temperature-sensitive lambda cl repressor functions on a modified operator in yeast cells by masking the TATA element", Molecular and General Genetics, 1995, vol. 248, pp. 499-505.

Ma et al., "Targeted gene suppression by inducing de novo DNA methylation in the gene promoter", Epigenetics & Chromatin, 2014, vol. 7, No. 20, pp. 1-11.

Sanber, K. S. et al., 'Construction of stable packaging cell lines forclinical lentiviral vector production', Scientific Reports, Mar. 12, 2015,vol. 5, article No. 9021, pp. 1-10.

Palmer et al., "Helper virus-mediated downregulation of transgene expression permits production of recalcitrant helper-dependent adenoviral vector", Molecular Therapy-Methods & Clinical Development, 2016, Year, vol. 3, No. 16039, pp. 1-6.

Reid et al., "MiRNA-mediated post-transcriptional silencing of transgenes leads to increased adeno-associated viral vector yield and targeting specificity", Gene Therapy, 2017, vol. 24, pp. 462-469.

Wang et al., "An shRNA Silencing a Non-Toxic Transgene Reduces Nutrient Consumption and Increases Production of Adenoviral Vectors in a Novel Packaging Cell", Journal Of Cellular Physiology, 2009, vol. 219, pp. 365-371.

Xie et al., "772. RNA Interference Mediated Ablation of Cytotoxic Transgenes Enables Productive Viral Vector Packaging", Molecular Therapy, 2017, vol. 25, No. 5S1, pp. 357-358.

Sanber et al., "Construction of stable packaging cell lines for clinical lentiviral vector production", Scientific Reports, 2015, vol. 5, No. 9021, pp. 1-10.

* cited by examiner

```
                         SEQUENCE LISTING

<160> NUMBER OF SEQ ID NOS: 12

<210> SEQ ID NO 1
<211> LENGTH: 45
<212> TYPE: DNA
<213> ORGANISM: Artificial Sequence
<220> FEATURE:
<223> OTHER INFORMATION: Synthetic laboratory-made recombinant nucleic
      acid

<400> SEQUENCE: 1
tatctctggc ggtgttgata taaataccac tggcggtgat atgca               45

<210> SEQ ID NO 2
<211> LENGTH: 45
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 2
acgtatagag accgccacaa ctatatttat ggtgaccgcc actat               45

<210> SEQ ID NO 3
<211> LENGTH: 126
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 3
aaatgggcgg taggcgtgta cggtgggagg tctatataag cagagctggt ttagtgaacc   60
gtcagatccg ctagagatct ggtaccgtcg acgcggccgc tcgagcctaa gcttgccacc  120
atggtg                                                             126

<210> SEQ ID NO 4
<211> LENGTH: 126
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 4
tttacccgcc atccgcacat gccaccctcc agatatattc gtctcgacca aatcacttgg   60
cagtctaggc gatctctaga ccatggcagc tgcgccggcg agctcggatt cgaacggtgg  120
taccac                                                             126

<210> SEQ ID NO 5
<211> LENGTH: 143
```

```
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 5
aaatgggcgg taggcgtgta cggtgggagg tctatctctg gcggtgttgt atataatacc    60
actggcggtg ataaaccgtc agatccgcta gagatctggt accgtcgacg cggccgctcg   120
agcctaagct tgccaccatg gtg                                            143

<210> SEQ ID NO 6
<211> LENGTH: 143
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 6
tttacccgcc atccgcacat gccaccctcc agatagagac cgccacaaca tatattatgg    60
tgaccgccac tatttggcag tctaggcgat ctctagacca tggcagctgc gccggcgagc   120
tcggattcga acgtggtac cac                                             143

<210> SEQ ID NO 7
<211> LENGTH: 126
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 7
aaatgggcgg taggctatct ctggcggtgt tgtatataat accactggcg gtgataaacc    60
gtcagatccg ctagagatct ggtaccgtcg acgcggccgc tcgagcctaa gcttgccacc   120
atggtg                                                               126

<210> SEQ ID NO 8
<211> LENGTH: 126
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 8
tttacccgcc atccgataga gaccgccaca acatatatta tggtgaccgc cactatttgg    60
cagtctaggc gatctctaga ccatggcagc tgcgccggcg agctcggatt cgaacggtgg   120
taccac                                                               126

<210> SEQ ID NO 9
<211> LENGTH: 140
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 9
tggtgatgcg gttttggcag tacatcaatg ggcgtggata gcggtttgac tcacggggat    60
ttccaagtct ccacccccatt gacgtcaatg ggagtttgtt ttggcaccaa aatcaacggg   120
```

```
actttccaaa atgtcgtaac                                            140

<210> SEQ ID NO 10
<211> LENGTH: 140
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 10
accactacgc caaaaccgtc atgtagttac ccgcacctat cgccaaactg agtgcccta    60 aaggttcaga ggtggggtaa ctgcagttac cctcaaacaa aaccgtggtt ttagttgccc  120
tgaaaggttt tacagcattg                                              140

<210> SEQ ID NO 11
<211> LENGTH: 140
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 11
aactccgccc cattgacgca aatgggcggt aggcgtgtac ggtgggaggt ctatataagc    60
agagctggtt tagtgaaccg tcagatccgc tagagatctg gtaccgtcga cgcggccgct  120
cgagcctaag cttctagata                                              140

<210> SEQ ID NO 12
<211> LENGTH: 140
<212> TYPE: DNA
<213> ORGANISM: Artificial Sequence
<220> FEATURE:
<223> OTHER INFORMATION: Synthetic laboratory made recombinant nucleic
      acid

<400> SEQUENCE: 12
ttgaggcggg gtaactgcgt ttacccgcca tccgcacatg ccaccctcca gatatattcg    60
tctcgaccaa atcacttggc agtctaggcg atctctagac catggcagct gcgccggcga  120
gctcggattc gaagatctat                                              140
```

MODIFIED EC7 CELLS HAVING LOW TOXICITY TO VIRAL PRODUCTION PAYLOADS

This application claims priority to U.S. provisional patent applications having Ser. No. 62/570,508, filed Oct. 10, 2017, and 62/633,412, filed Feb. 21, 2018, both incorporated by reference herein.

SEQUENCE LISTING

The content of the following submission on ASCII text file is incorporated herein by reference in its entirety: a computer readable form (CRF) of the Sequence Listing (file name: 102538.0048_ST25.txt, date created: May 3, 2021, size: 4.15 KB).

FIELD OF THE INVENTION

The field of the invention is recombinant cells, and especially modified mammalian cells used for production of therapeutic recombinant viruses used for cancer vaccines.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Gene therapies using a virus as delivery system for a recombinant therapeutic protein, and protein production in mammalian cells have become more and more accepted in the art. While at least conceptually relatively simple, various difficulties have been encountered, and most of the problems were associated with the virus-host interaction.

For example, adenoviruses are well-characterized dsDNA viruses and often allow for the production of adenovirus particles that contain various transgenes for delivery to many cell types of interest. Adenovirus type 5 represents one of the best studied platforms in this regard, with numerous kits available in the commercial space to produce user-determined viruses. Adenovirus type 5 produced in this manner have been used in cell culture, animal, and even clinical trials, further supporting the familiarity of scientific and clinical practitioners with this system. Entry of the virus into the cell is thought to be mediated via the Coxsackie and Adenovirus receptor (CXADR). Therefore, cells or tissues failing to produce CXADR have limited use of the Adenovirus type 5 technology in such cells, and so prevent transduction of many clinically relevant cells and tissues, including stem cells and immune cells.

CXADR (Swiss-Prot Accession Number: P78310) is a type I membrane receptor and a member of the immunoglobulin superfamily (Science (1997) 275; 1320-1323). CXADR has an extracellular domain that is typically larger than 200 amino acids in size and is believed to be a component of the epithelial apical junction complex essential for the tight junction integrity (J Biol Chem (1999) 274; 10219-10226). CXADR can be overexpressed in host cells to so gain an entryway for the AD5 virus. While such recombinant cells are sensitive to Ad5 transfection, and possibly improved protein production, such systems will still suffer from various drawbacks. Most notably, where the virus is used as a therapeutic entity, generation of sufficient quantities of recombinant viruses (e.g., $10^{10}$-$10^{12}$ viral particles) is often inconsistent and in some cases not even achievable.

Improvements in viral titers have, for example, been previously reported for some adeno-associated viruses by regulation of expression of REP and CAP proteins of an adeno-associated virus as was reported in U.S. Pat. No. 6,548,286, WO 98/46728, or US 2004/0043490. However, such systems will generally not translate to other viral systems due to the specificity of the REP and CAP proteins of the adeno-associated virus and life cycle of such virus. In another approach, where protein production in a production cell from a recombinant nucleic acid was driven from a recombinant gene expressed in a CHO cell, the cells were cultured in the presence of a synthetic siRNA to suppress expression of the recombinant protein, and later in the absence of the siRNA to allow for production of the desired recombinant protein as disclosed in U.S. Pat. No. 8,273,722. However, while such systems increase to at least some degree quantities of a desired recombinant protein, generation of high titers of recombinant viruses was neither contemplated nor even feasible in the described CHO cells.

Therefore, while numerous cell production systems and viral vectors are known in the art, there remains a need for systems and methods to produce high titers of recombinant viruses, and especially therapeutic viruses in a simple and effective manner.

SUMMARY OF THE INVENTION

The inventive subject matter is directed to compositions and methods of producing high titers of recombinant viruses, and especially recombinant Adenovirus type 5 that contain one or more nucleic acid segments encoding a therapeutic protein (e.g., tumor associated antigen, tumor neoepitope, polytope, etc.).

In one aspect of the inventive subject matter, the inventors contemplate a method of producing a plurality of recombinant therapeutic viruses that includes a step of providing a recombinant host cell (e.g., CHO cell or an EC7 cell) that expresses CXADR (e.g., from a recombinant nucleic acid sequence) and that is genetically modified to express a recombinant entity that reduces expression of a viral payload gene in the recombinant host cell; and a further step of transfecting the recombinant host cell with a recombinant virus that comprises a nucleic acid sequence encoding the viral payload gene (e.g., cytokine, chimeric protein, tumor associated antigen, neoepitope, etc.). In a still further step, the transfected host cell is cultured under conditions that reduce the expression of the viral payload gene in the host cell and that produce at least a predetermined viral titer. Most typically, but not necessarily, the recombinant virus is an adenovirus, and especially an E2b-deleted adenovirus type 5.

While in some aspects the recombinant entity is a protein (e.g., a transcriptional repressor that binds to a binding site on the recombinant virus, with the binding site being in an enhancer/promoter sequence, 5'UTR sequence, an IRES sequence, or a 3'-UTR sequence), the recombinant entity may also be a nucleic acid (e.g., siRNA, shRNA, antisense- RNA, or catRNA that binds to a binding site on an RNA of the recombinant virus such as in a 5'UTR sequence, an IRES sequence, or a 3'-UTR sequence).

It is further contemplated that the predetermined viral titer is at least $10^8$ or $10^9$ viral particles/ml, and/or that the predetermined viral titer is reached within a time period having a variability of equal or less than 20%, and more preferably equal or less than 10% among different recombinant viruses having different viral payload genes.

In another aspect of the inventive subject matter, the inventors contemplate a method of producing a plurality of recombinant therapeutic viruses that include a step of providing a host cell that expresses an entity that reduces expression of a viral payload gene in the host cell, and a further step of transfecting the host cell with a recombinant virus that comprises a nucleic acid sequence encoding the viral payload gene, and that further comprises a sequence that binds the entity or that encodes a sequence that has a binding site on an RNA of the recombinant virus for the entity. In a still further step, the transfected host cell is cultured under conditions that reduce the expression of the viral payload gene in the host cell and that produce at least a predetermined viral titer. Most typically, but not necessarily, the recombinant virus is an adenovirus, and especially an E2b-deleted adenovirus type 5, and the host cell is a CHO cell or an EC7 cell (HEK293 cell expressing adenoviral polymerase) which may express CXADR, optionally from a recombinant nucleic acid sequence.

Where desirable, the host cell expresses the entity from a recombinant nucleic acid, or the entity is an entity that is naïve to the host cell (e.g., protein or RNA). Likewise, it is contemplated that the sequence in the recombinant virus need not be naïve to the recombinant virus.

In a further aspect of the inventive subject matter, the inventors also contemplate method of producing a plurality of recombinant therapeutic viruses that includes a step of providing a host cell that genetically engineered to conditionally expresses an entity that reduces expression of a viral payload gene in the host cell; and a another step of transfecting the host cell with a recombinant virus that comprises a nucleic acid sequence encoding the viral payload gene, and that further comprises a sequence that encodes a signaling sequence that triggers conditional expression of the entity in the host cell. In yet another step, the transfected host cell is cultured under conditions that reduce the expression of the viral payload gene in the host cell and that produce at least a predetermined viral titer.

As noted before, it is contemplated that the host cell may expresses CXADR, optionally from a recombinant nucleic acid, and that the entity is a DNA or RNA binding protein, or an RNA. Moreover, it is contemplated that the signaling sequence that triggers conditional expression encodes a transcription factor.

In still another aspect of the inventive subject matter, the inventors contemplate a method of producing a plurality of recombinant therapeutic viruses that includes a step of providing a host cell that genetically engineered to expresses a first portion of a co-repressor that reduces expression of a viral payload gene in the host cell; and another step of transfecting the host cell with a recombinant virus that comprises a nucleic acid sequence encoding the viral payload gene, and that further comprises a second portion of the co-repressor, and wherein the nucleic acid sequence encoding the viral payload gene is under control of the co-repressor. In yet another step, the transfected host cell is cultured under conditions that reduce the expression of the viral payload gene in the host cell and that produce at least a predetermined viral titer.

Additionally, the inventors also contemplate a method of producing a plurality of recombinant therapeutic viruses that includes a step of providing a host cell that is optionally engineered to lack expression of interferon gamma upon infection with a virus; and a further step of transfecting the host cell with a recombinant virus that comprises a nucleic acid sequence encoding the viral payload gene, wherein the nucleic acid sequence encoding the viral payload gene is under control of an interferon regulatory factor (e.g., via an IFN-stimulated response element). In yet another step, the transfected host cell is cultured under conditions that produce at least a predetermined viral titer.

Consequently, the inventors also contemplate a genetically engineered cell that comprises a recombinant nucleic acid encoding an entity that reduces expression of a viral payload gene in a host cell transfected with a recombinant virus, wherein the entity binds to a binding site on an RNA of the recombinant virus.

Contemplated genetically engineered cells may also comprise a recombinant nucleic acid encoding an entity that reduces expression of a viral payload gene in a host cell transfected with a recombinant virus, wherein the recombinant nucleic acid is under control of a protein or nucleic acid encoded by the recombinant virus.

Similarly, contemplated genetically engineered cell may comprise a recombinant nucleic acid encoding a first portion of a co-repressor that reduces expression of a viral payload gene in the cell when the cell is transfected with a recombinant virus comprising a nucleic acid encoding the payload.

Additionally, the inventors further contemplate a genetically engineered cell that is modified to lack expression of interferon gamma upon infection with a virus.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 15 depicts an exemplary construct that has an IE86 responsive cis repression sequence (crs) downstream of a promotor to suppress transcription.

DETAILED DESCRIPTION

Figure 1:
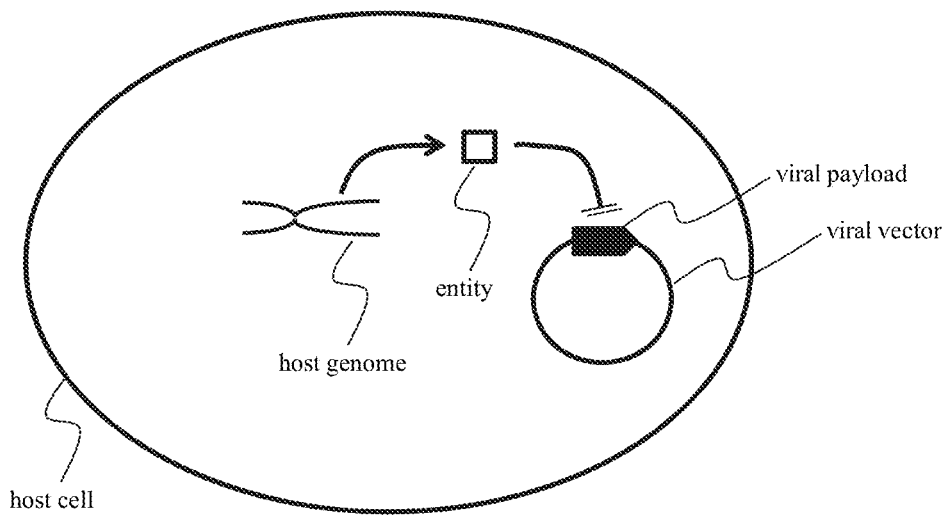
FIG. 1 depicts a first exemplary expression system according to the inventive subject matter.

The inventive subject matter provides recombinant cells, systems, and methods for the production of recombinant viral therapeutics, and especially for the production of high-titers of recombinant Ad5 virus in a manner that provides a consistent performance envelope across a large variety of viruses that are distinguished by their recombinant payload (e.g., tumor associated antigens, neoepitopes (that may be arranged in a polytope), immune regulatory molecules, co-stimulatory molecules, etc.). Such recombinant cells, systems, and methods will advantageously allow production of desirably high titers of the virus independent of the recombinant payload, typically in a reproducible and predictable time frame. Viewed form another perspective, contemplated recombinant cells, systems, and methods enable reliable production of therapeutic viruses regardless of the recombinant payload, and further allow massively parallel production of multiple and distinct therapeutic viruses under a common production schedule and production environment.

Thus, systems and methods provided herein will therefore be particularly suitable for multiplexed production of recombinant therapeutic viruses at high yields. Such advantages are achieved by reducing, or even entirely eliminating expression of the recombinant payload in the host cell (viral production cell) using various approaches. While not limiting to the inventive subject matter, it is generally preferred that the host cells used for production are genetically engineered to reduce, or even entirely eliminate the expression of the recombinant payload in the host cell to so enable 'drop-in replacement' of patient specific viral payloads into a prefabricated 'generic' therapeutic viral vector.

As will be readily appreciated, there are numerous therapeutic viruses known in the art and all of those are deemed suitable for use herein. For example, contemplated therapeutic viruses include enveloped viruses such as retroviruses, lentiviruses, or HSV-1, as well as non-enveloped viruses such as adeno-associated viruses and adenoviruses (that may be of human or non-human origin, having various serotypes). Consequently, various host cells are also deemed suitable, and the choice of therapeutic virus will at least to some degree determine the choice of a host cell. Furthermore, it should be appreciated that host cells may also be genetically modified to so accommodate infection and/or propagation of a virus that would otherwise not be suitable for such cells without genetic modification. However, especially preferred therapeutic viruses include adenoviruses of human and non-human (e.g., primate) origin.

For example, in one preferred aspect of the inventive subject matter, the therapeutic virus is a replication deficient adenovirus type 5 that includes as a payload at least one of a patient and tumor specific neoepitope sequence, a tumor associated antigen, a cytokine, a superkine (e.g., ALT803), a chimeric protein (e.g., having a scFv domain as a target binding portion and an effector portion to provide a desired biological effect), a co-stimulatory molecule, a checkpoint inhibitor, and a chemokine. In further preferred examples, CHO or HEK293 cells are employed as host cells for virus propagation. However, CHO and HEK293 cells do not normally express detectable amounts levels of the coxsackie/adenovirus receptor (CXADR) and are thus generally inefficiently transduced by adenovirus type 5. Therefore, it should be noted that such (and other cells lacking CXADR expression) can be genetically modified to express a recombinant CXADR. Moreover, CHO and HEK293 cells also do not normally express the E1 gene of Ad5, and will therefore be further genetically modified to express and provide E1 protein function in trans where a replication deficient Ad5 virus is employed. Such complementation is particularly desirable where the adenovirus has a further deletion in the E2b gene (see e.g., *J Virol*. 1998 February; 72(2):926-33), and such adenoviruses are particularly preferred.

Thusly modified host cells will provide a window for viral entry and delivery of the viral expression vector into the host cell. More specifically, the inventors discovered that CHO cells can be modified to express CXADR and so become susceptible to viral infection by Type 5 adenoviruses. Indeed, the inventors also found that E2b-deleted adenoviruses bearing biologic cargo introduced into CHO cells expressing CXADR (CAR-CHO cells) resulted in robust, long term production of the progeny viruses. This result suggests that CAR-CHO cells may serve as a universal production system for therapeutic viruses, which will significantly decrease their production times and costs. This system is also predicted to be compatible with long-term continuous culture systems for commercial production. Moreover, systems and methods contemplated herein can even be adapted to continuous production of various distinct biologics with minimal manipulation of intermediates.

For example, in one aspect of the inventive subject matter, a cDNA encoding CXADR can be cloned into a suitable expression plasmid (e.g., peak8-puromycin plasmid), with the gene expression driven from a strong promoter (e.g., EF-1α promoter). Of course, various other promotor elements (that may be inducible or constitutive) are also deemed suitable for use herein. The transgene sequence can be verified by DNA sequencing and aligned with, for example, the published sequence for CXADR isoform 1 in the reference data set (NP_001329.1). The expression plasmid is then transfected into CHO cells using standard transfection protocols as is well known in the art. Selection of transfected cells for preparation of a cell stock can then be performed using puromycin. Likewise, it should be appreciated that the inventive subject matter is not limited to a specific expression vector, and that indeed all manners of expression from a nucleic acid in a cell are deemed suitable for use herein. For example, where transient expression is desired, the nucleic acid may be delivered as RNA or as circular extrachromosomal DNA without eukaryotic replication sequence. On the other hand, where permanent expression is desired, or where a cell line for large scale production of multiple distinct batches of therapeutic viruses is needed, the nucleic acid may be delivered for integration into the cell's genome, or the cell may be subject to genome editing (e.g., using CRISPR/Cas9 technology) to so install an expression cassette into the genome of the host cell.

Likewise, it should be appreciated that the transcription and translation control of the CXADR gene may vary considerably, and the proper choice of suitable control elements will be readily apparent to the skilled artisan. Thus, expression may be driven from constitutively active promoters, from inducible promoters using corresponding inducing agents, or from a promoter that is activated under selected tissue or culture conditions. For example, expression may be driven under the control of a temperature sensitive promoter (e.g., *BMC Biotechnol.* 2011; 12; 11:51) or under control of a hypoxia and metal sensitive promoter (see e.g., *Gene Ther.* 2006; 13(10):857-68). Thus, it should be appreciated that cells suitable for production of therapeutic viruses that are otherwise not susceptible to adenovirus transfection can be rendered sensitive to infection, and with that to large scale production of delivery of therapeutic viruses. Of course, it should be appreciated that the same considerations also apply to the recombinant expression (where needed) of a viral polymerase to compensate for the lack of that enzyme where a replication deficient virus is employed. Exemplary preferred recombinant adenoviruses and cells with a viral polymerase are described elsewhere.

With respect to suitable viral expression vectors, it is contemplated that numerous viral expression vectors appropriate. However, and as noted above, it is especially preferred that the viral expression vector is an adenoviral expression vector, and particularly from which the E1, E2b, and E3 genes had been deleted (e.g., *J Virol.* 1998; Vol. 72(2): p 926-933). Notably, the inventors have observed that the efficient protein expression of the viral payload in recombinant cells as described above may interfere with production of high titers of viral particles, especially where production of therapeutic quantities of recombinant virus is desired. For example, in at least some experiments, viral titers of less than $10^7$ viral particles/ml, or even less than $10^6$ viral particles/ml, or even less than $10^5$ viral particles/ml were observed with some recombinant payload (or entirely failed to produce any meaningful viral titer), while the same viral system did produce viral titers of more than $10^7$ viral particles/ml, or more than $10^8$ viral particles/ml (and higher) with other recombinant payloads. Moreover, where multiple different virus preparations for multiple different patients were prepared, significant time delays between preparations to reach a desired quantity of viral particles (e.g., $10^{11}$ total viral particles) were observed, which will prevent many therapeutic virus production schemes that require synchronicity between different preparations.

The inventors have now discovered that such high-titer viral production problems can be overcome by modifying at least one of the host cell and the viral genome to reduce or even eliminate interference of protein production of the viral payload with the overall yield and/or time to produce therapeutic amounts of a virus, regardless of the type and/or length of the viral payload. Most typically, the host cell can be modified to produce an entity that directly or indirectly interferes with transcription and/or translation and/or mRNA stability of a gene that is encoded on the viral nucleic acid. Such approach is especially desirable as in at least some embodiments (where the entity targets a sequence common to different viruses) a single batch of host cells can serve as a viral production platform for a wide variety of recombinant therapeutic viruses without the need to reengineer the virus. On the other hand, both host cell and viral vector may contribute to a gene transcription and/or translation inhibition and/or mRNA stability that is exclusive to their (specific) combination. In still other examples, the host cell may be genetically engineered to lack a transcription factor needed to express a payload gene. Most preferably, the recombinant virus will be engineered such that the suppression of expression of the recombinant payload only occurs in the host cell but not in a patient cell.

Figure 2:
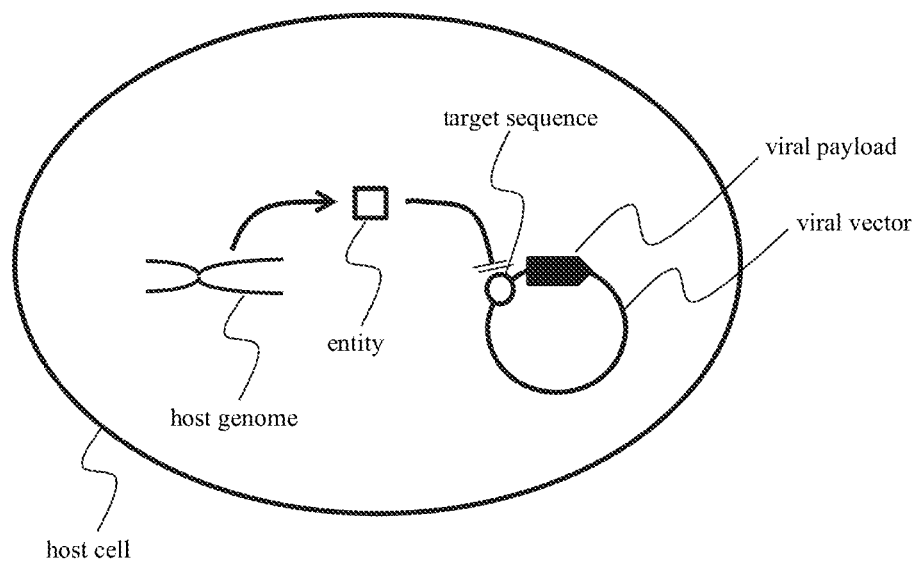
FIG. 2 depicts a second exemplary expression system according to the inventive subject matter.

For example, as schematically illustrated in FIG. 1, a host cell may be selected and/or genetically engineered to include a gene that encodes an entity that directly interferes with the expression of a viral payload (e.g., recombinant gene used for therapy, such as neoepitope, co-stimulatory molecule, checkpoint inhibitor, cytokine, etc.) present on the viral vector. Among other suitable entities encoded in the host cell (and especially in the host genome), especially contemplated entities include selected proteins and RNA. For example, where the entity is a protein, the protein may bind to a binding site on the viral vector that controls transcription of the viral payload or the protein may bind to translation initiation site or ribosome binding site or IRES of a RNA encoding the payload. Similarly, the protein may also bind to the transcription initiation site of the sequence preceding the payload sequence. In some embodiments, the entity can be an interacting protein to a peptide encoded by the payload gene, and the interaction between the entity and the peptide induces the degradation or inactivation of the peptide. In another example, where the entity is a nucleic acid, especially preferred nucleic acids include siRNA, shRNA, anti-sense-RNA, and/or catRNA that bind to a mRNA encoding the payload so prevent translation and/or destabilize the mRNA of the payload as is further shown in more detail below. Of course, the entity may also be externally supplied to the host cell (e.g., via various methods such as transfection, lipofection, electroporation, etc.)

Where binding sites are not available on the mRNA encoding the payload, inhibition may be performed indirectly by engineering a binding sequence into the mRNA encoding the payload that is preferably immediately upstream of the coding region (e.g., in the 5'-UTR region, or in the translation initiation region) of the payload as is exemplarily depicted in FIG. 2. However, in alternative aspects, the binding site for the entity may also be at or near an IRES or 2A site, and/or in a 3'-UTR of the mRNA. As noted before, suitable entities will include nucleic acids as well as proteins. Such approach may be particularly beneficial as the target sequence on the viral vector may be purpose-selected and placed in the proper context to achieve inhibition of translation via RNA destabilization, for example, using siRNA or shRNA (which may be transcribed from the host cell genome as is further shown in more detail below or transfected into the host cell).

Figure 3:
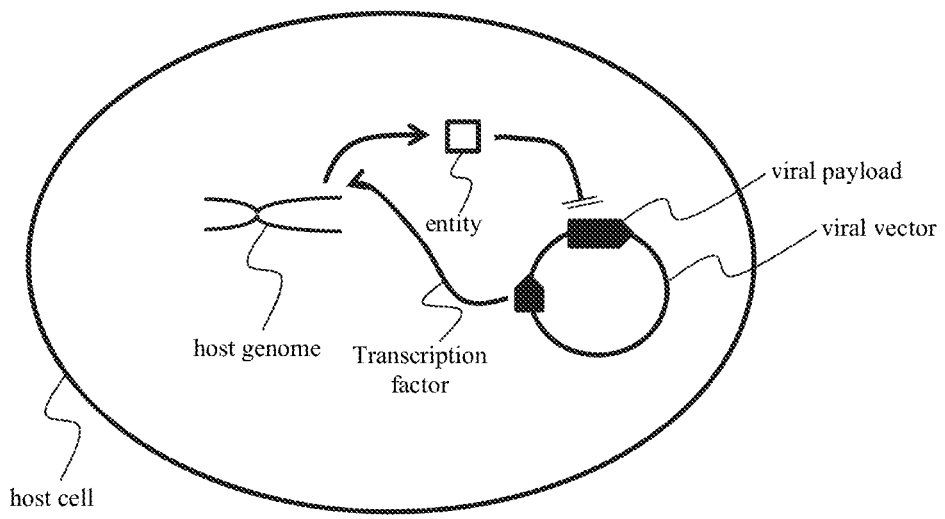
FIG. 3 depicts a third exemplary expression system according to the inventive subject matter.
Figure 4:
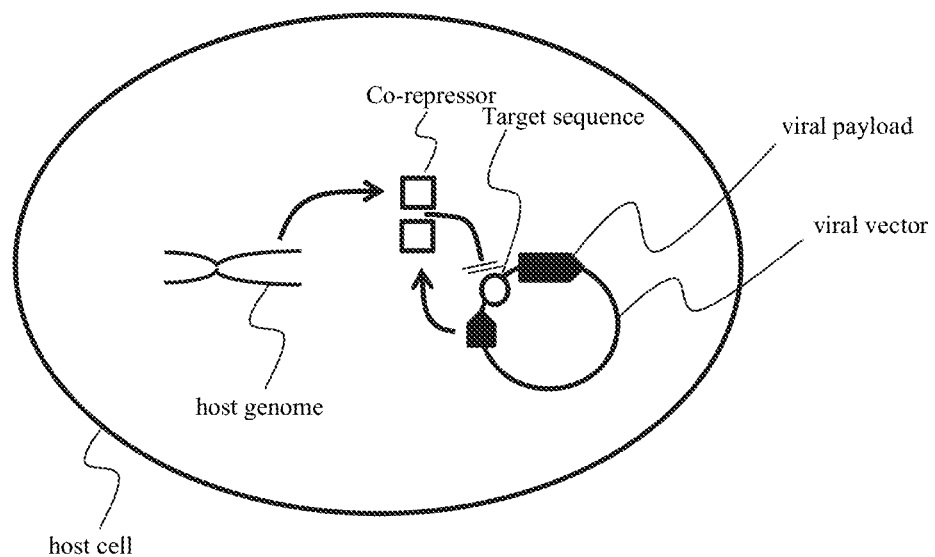
FIG. 4 depicts a fourth exemplary expression system according to the inventive subject matter.

In still another exemplary aspect of the inventive subject matter, as schematically shown in FIG. 3, the viral vector may encode a regulatory protein (e.g., transcription factor), that induces expression of a gene on the host cell genome (or recombinant nucleic acid in the host cell) that in turn leads to the production of an entity as described above that will inhibit or reduce transcription and/or translation and/or mRNA stability of the viral payload, directly or indirectly (as seen in FIGS. 1 and 2). Thus, in such example, it should be appreciated that the expression of the entity is conditional upon the presence of the recombinant viral nucleic acid. Such conditional expression is believed to be especially advantageous as the host cells can be grown to considerable density without interference of the inhibition system as could potentially be the case in the systems of FIGS. 1 and 2. Similarly, FIG. 4 schematically illustrates yet another cooperative approach between the host cell and the viral nucleic acid in which one portion of a co-repressor is encoded by the host cell's genome (or other recombinant nucleic acid in the cell) while the other portion is encoded on the recombinant viral nucleic acid. Thus, in such systems, inhibition of expression of the payload is again conditional on the presence of a regulatory gene in the host cell.

Figure 5:
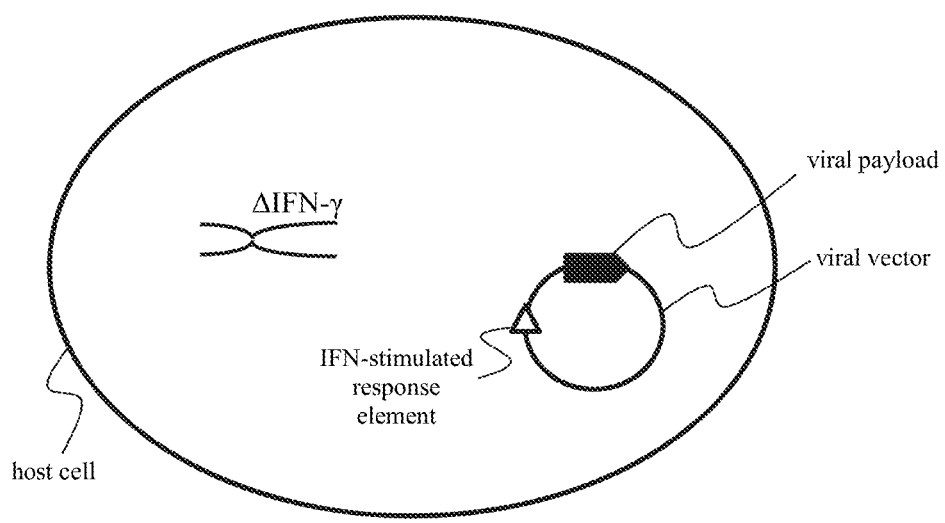
FIG. 5 depicts a fifth exemplary expression system according to the inventive subject matter.
Figure 6:
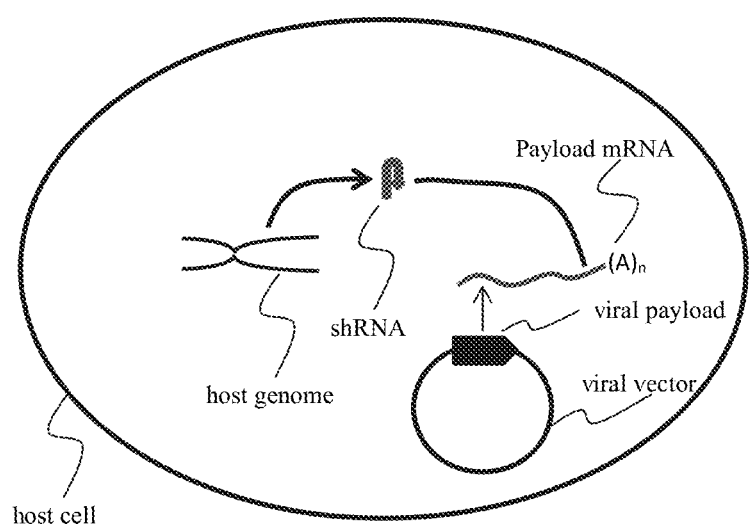
FIG. 6 depicts a sixth exemplary expression system according to the inventive subject matter.

FIG. 5 schematically illustrates yet another system in which expression of the payload in the recombinant viral nucleic acid is conditional upon presence of a factor that is not present or abolished in the host cell. In the example of FIG. 5, the host cell is genetically modified (e.g., via targeted deletion, site directed mutagenesis, genome editing, etc.) to not produce interferon gamma in response to viral infection, and the nucleic acid of the virus is configured such that the payload is only expressed in the presence of interferon gamma, which can be achieved by use of an IFN-stimulated response element upstream of the payload. On the other hand, as schematically illustrated in FIG. 6, the host cell is genetically modified to produce an shRNA that will not interfere with cellular processes of the host cell, but that suppresses translation of the recombinant RNA that is produced from the viral vector. Such shRNA may be provided from the modified host cell genome or from a recombinant plasmid in the host cell.

In addition, it should be appreciated that the sequences relevant for inhibition need not be limited to sequences present in the host genome (naïve or via genetic engineering) but may also be provided by sequences on a recombinant plasmid or adeno-associated virus that co-infects the cell where the recombinant virus with the payload is an adenovirus. Consequently, host cells may be a genetically engineered cell that comprises a recombinant nucleic acid encoding an entity that reduces expression of a viral payload gene in a host cell transfected with a recombinant virus, wherein the entity binds to a binding site on an RNA of the recombinant virus. Likewise, contemplated cells may also be engineered to include a recombinant nucleic acid encoding an entity that reduces expression of a viral payload gene in a host cell that is transfected with a recombinant virus, wherein the recombinant nucleic acid is under control of a protein or nucleic acid encoded by the recombinant virus. In yet further contemplated aspects, the genetically engineered cell may also comprise a recombinant nucleic acid encoding a first portion of a co-repressor that reduces expression of a viral payload gene in the cell when the cell is transfected with a recombinant virus comprising a nucleic acid encoding the payload, or be modified to lack expression of interferon gamma upon infection with a virus Regardless of the manner of suppressing expression of the payload of the recombinant virus, it is contemplated that suitable systems will afford a significantly improved uniformity in terms of yield and/or production time required to reach a predetermined quantity of therapeutic viral particles irrespective of the content and/or size of the payload. For example, the variability of time needed between different virus preparations to reach a predetermined target titer or total quantity of virus particles (e.g., at a target titer of at least $10^9$ viral particles/ml, or a target total quantity of at least $10^{11}$ viral particles) is contemplated to be equal or less than 20%, more preferably equal or less than 15%, or equal or less than 10%, or equal or less than 5%. Likewise, the titer or total number of viral particles at a predetermined production time (e.g., after 6 hours, or after 8 hours, or after 12 hours, or after 18 hours, or after 24 hours, or after 36 hours, etc.) will typically vary by no more than 20%, more preferably no more than 15%, or no more than 10%, or no more than 5%.

Therefore, contemplated systems and methods will be particularly advantageous in virus production environments where multiple and distinct viral preparations are prepared in multiplex or synchronous processes that require, for example, coordinated processing steps such as viral stock or cell stock addition, media addition, cooling, centrifugation or filtration, packaging, etc.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

EXAMPLES

Figure 7:
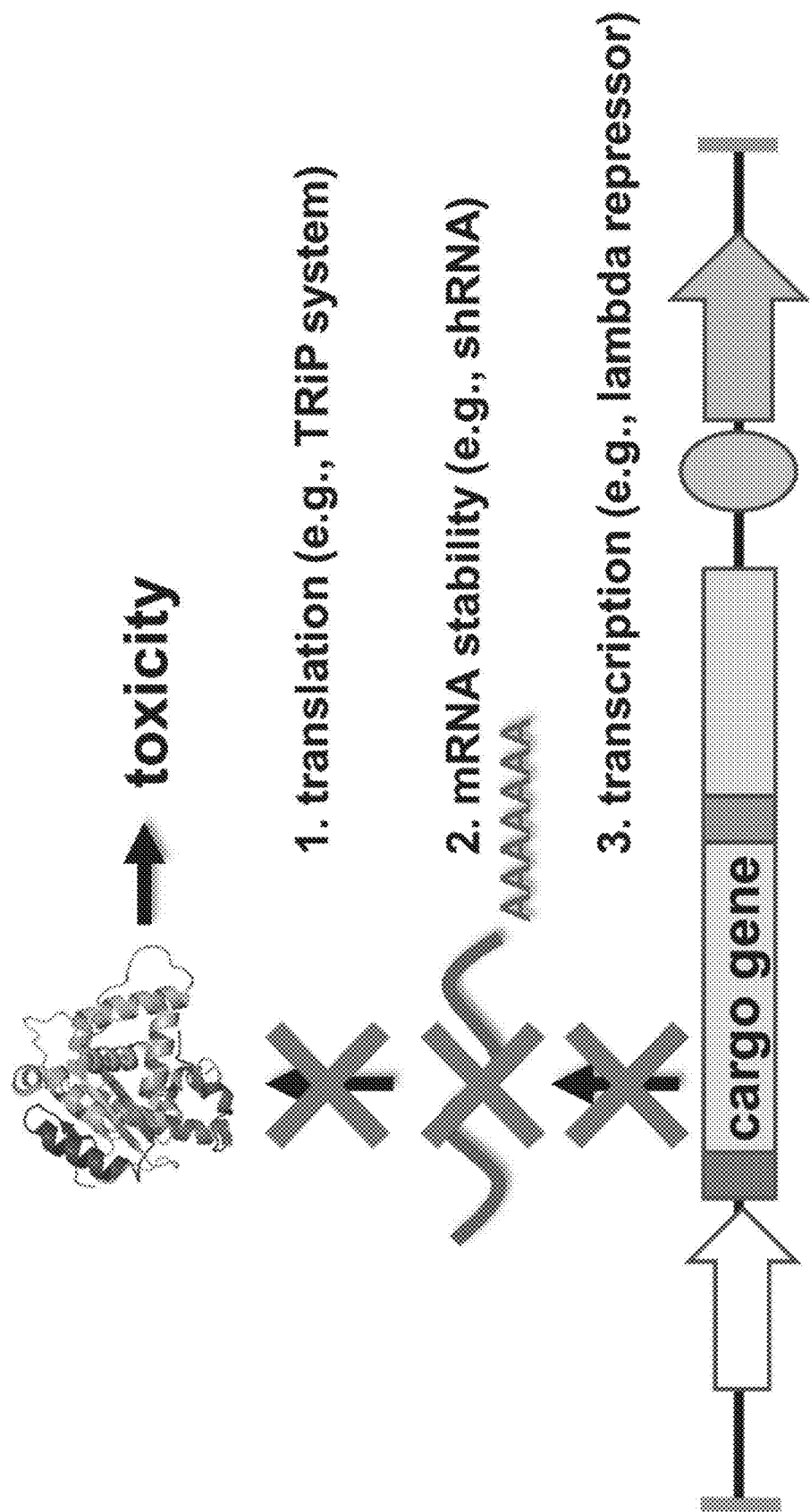
FIG. 7 depicts exemplary options for suppression of expression of recombinant payload in a recombinant virus.

FIG. 7 depicts exemplary options for the suppression of expression of the recombinant payload in a recombinant virus in which the translation of the mRNA can be suppressed, for example, using a TRIP system (see e.g., NATURE COMMUNICATIONS 18:14834 DOI: 10.1038/ncomms14834), or in which stability of the mRNA can be reduced as is described in more detail below, or in which transcription of the DNA segment encoding the payload is reduced or blocked as is also described in more detail below.

Figure 8:
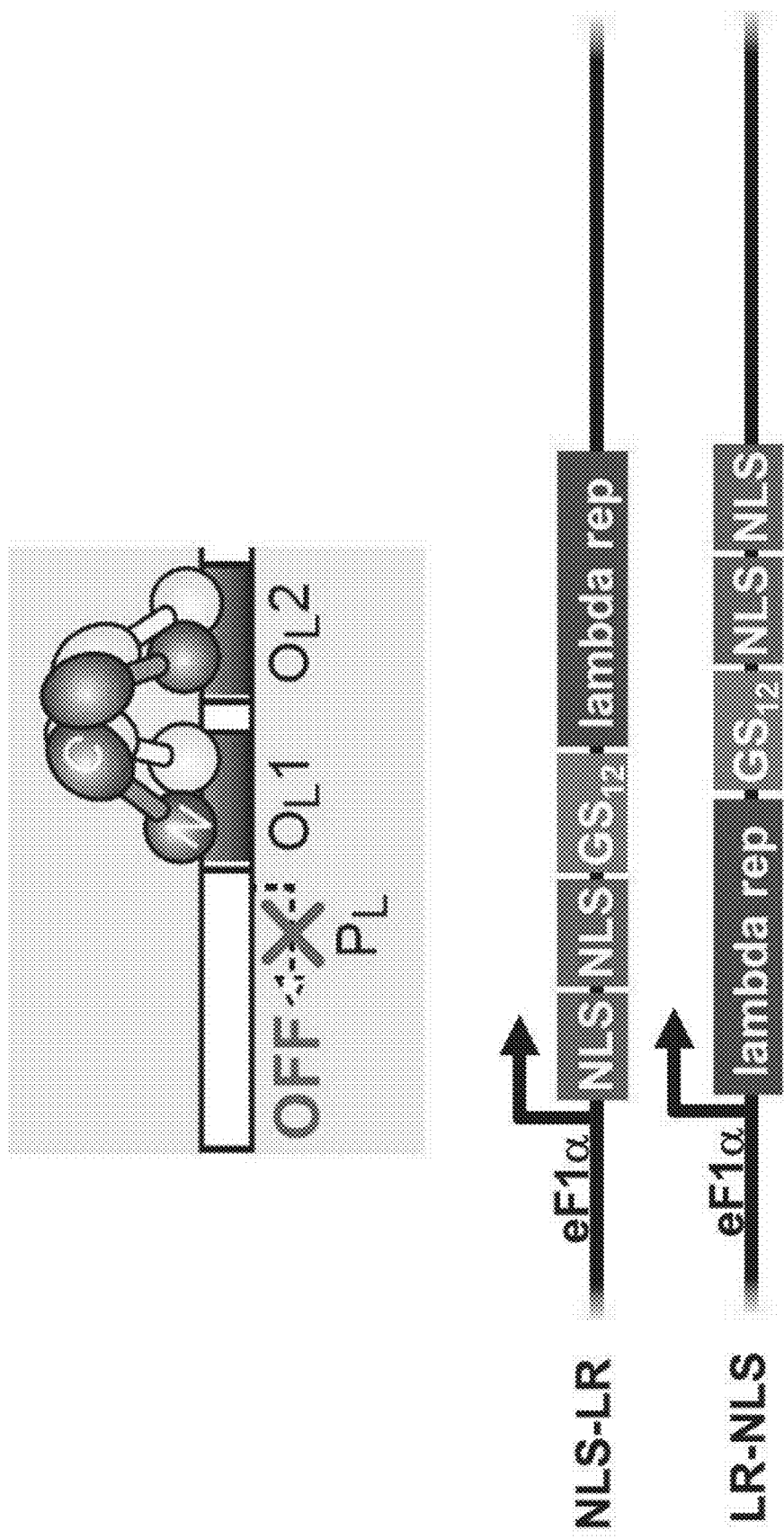
FIG. 8 depicts exemplary genetic modifications of a host cell to produce a nuclear localized lambda repressor.

For example, in one exemplary approach to suppress transcription, the inventors used the lambda repressor and corresponding operator sequence in combination with the gene of interest as is schematically depicted in the top panel of FIG. 8. Here, the recombinant nucleic acid has two operator (repressor binding) sequence portions $O_L1$ and $O_L2$ to which dimeric lambda repressors are bound. Once the repressor is bound, transcription from the promotor $P_L$ is suppressed as indicated by the crossed-out dashed arrow. As the operator/repressor are operable in bacteria, use in eukaryotic systems typically requires a nuclear location sequence to allow transfer of the lambda repressor into the nucleus. In the present example, the nuclear location sequence was encoded in frame with an intervening flexible linker (here: GS linker) either upstream or downstream of the ORF for the lambda repressor as schematically shown in the two lower sketches of FIG. 8 where NLS is the nuclear location sequence, GS12 is the flexible linker, and lambda rep is the lambda repressor. Expression of the fusion protein can be driven from various promotors as will be readily appreciated. In the present example, the eF1α promotor was employed, and the lambda repressor was expressed from an expression vector in EC7 cells.

Figure 9:
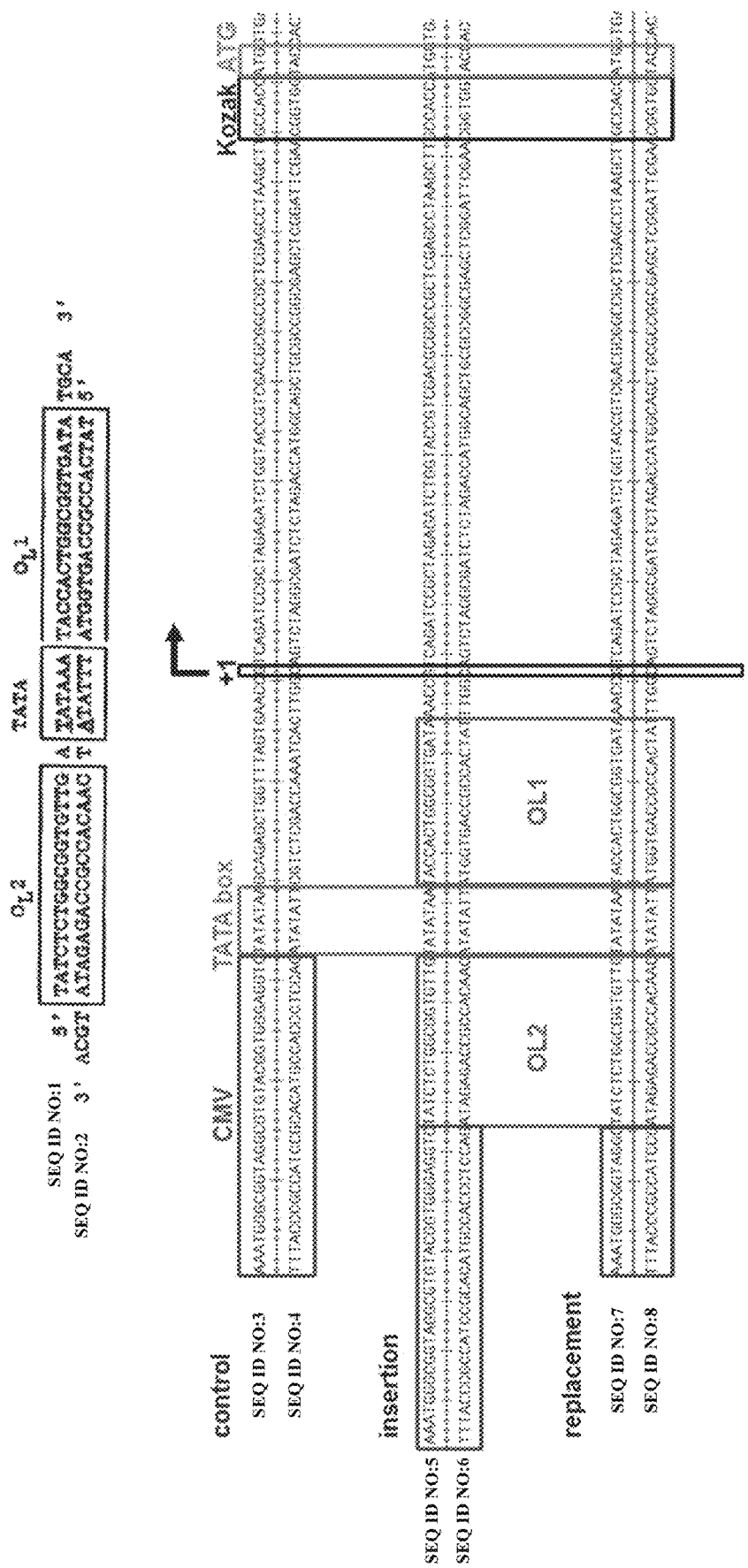
FIG. 9 depicts exemplary genetic modifications of a recombinant virus that include operator sequences capable of binding the lambda repressor.
Figure 10:
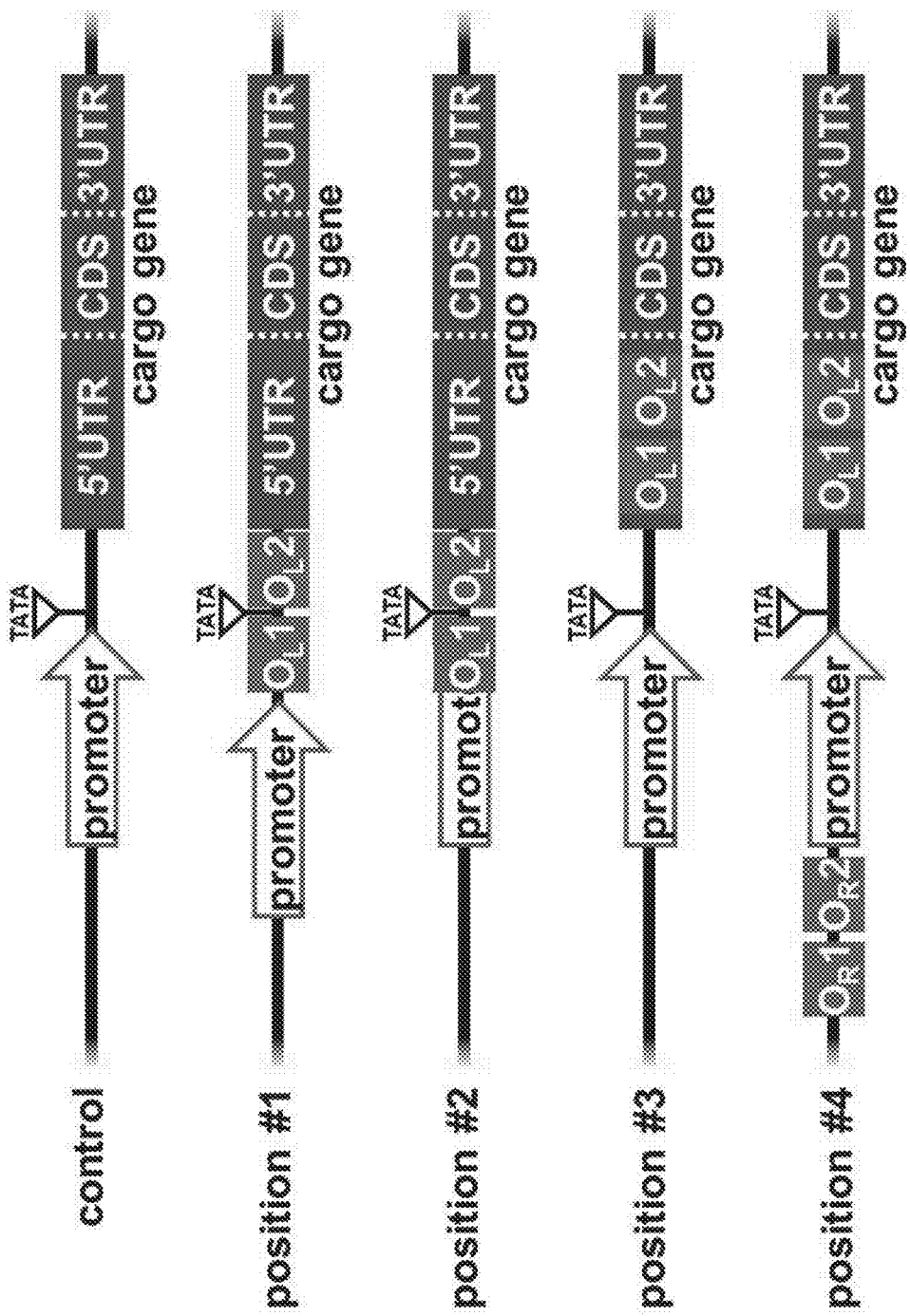
FIG. 10 depicts further exemplary genetic modifications of a recombinant virus with operator sequences capable of binding the lambda repressor.

Control of the gene of interest (here: GFP) was realized by placing operator sequence elements OL1 and OL2 just upstream of the transcription start (indicated with +1) that also included a TATA box upstream of the transcription start and a Kozak sequence downstream of the transcription start, followed by the start codon ATG as exemplarily shown in FIG. 9. Here, the positive control sequence had no operator sequence elements OL1 and OL2 and comprised the CMV promotor, the TATA box, the transcription start site, a Kozak sequence, and the start codon. Placement of the operator sequence elements OL1 and OL2 was then tested in two positions: by insertion of OL1 and OL2 between the end of the CMV promoter sequence and the transcription start (straddling the TATA box), or by replacement of the terminal portion of the CMV promoter sequence (straddling the TATA box). FIG. 10 further depicts alternative placements of the operator sequence elements OL1 and OL2, with further indication of 5'- and 3'-untranslated sequences, where CDS denotes the coding sequence of the gene of interest.

Figure 11:
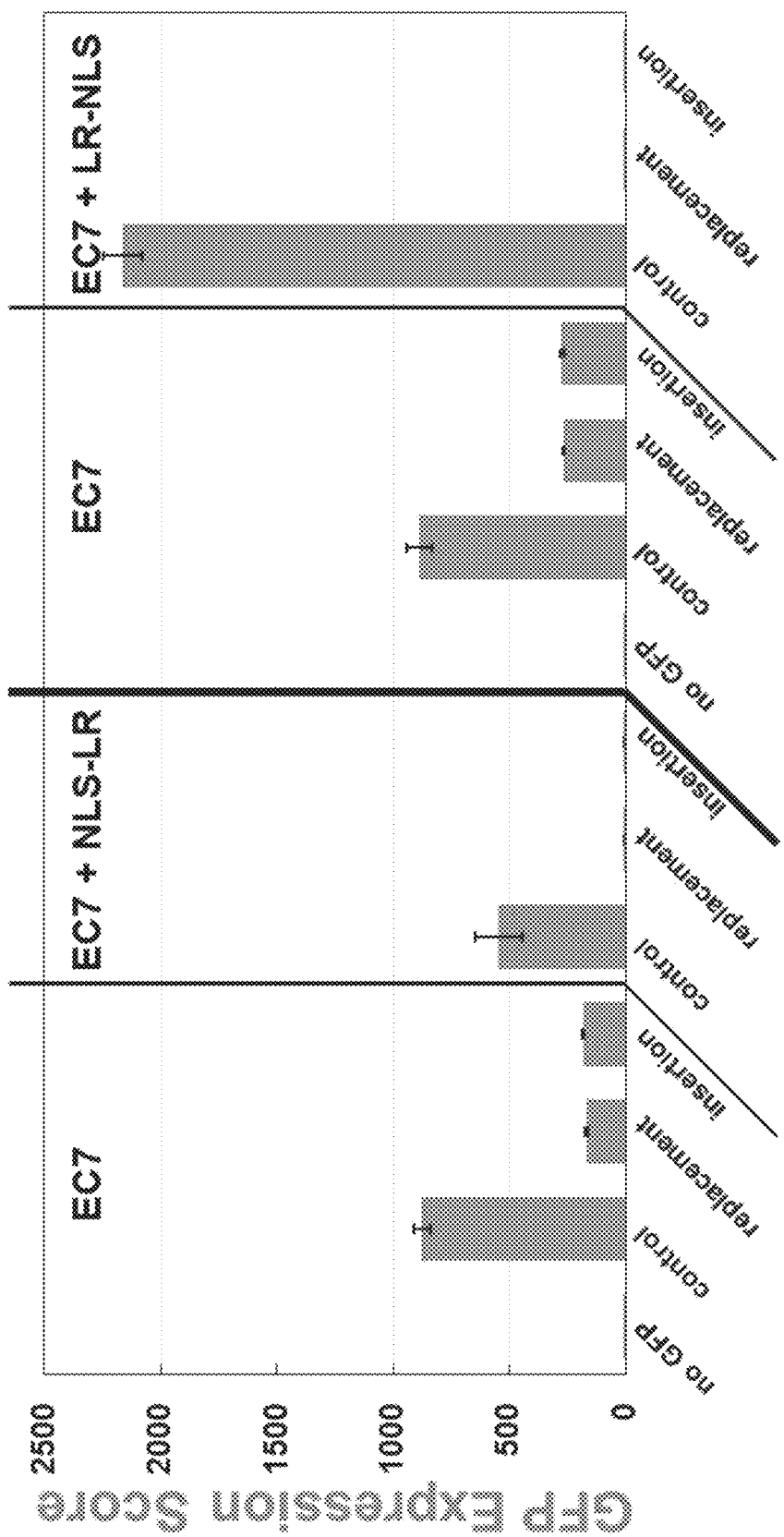
FIG. 11 depicts exemplary results for suppression of expression of a reporter gene from a recombinant virus with operator sequences capable of binding the lambda repressor.

FIG. 11 depicts exemplary results for transfected EC7 host cells that expressed lambda repressor with a leading (NLS-LR) or trailing (LR-NLS) nuclear location sequence expressed from an expression plasmid. The recombinant EC7 cells were also transfected with a second recombinant expression plasmid carrying (a) no GFP gene, (b) GFP gene without operator sequence elements, (c) the GFP gene with operator sequence elements that replaced part of the end of the CMV promoter sequence as shown in FIG. 9, and (d) the GFP gene with operator sequence elements that inserted after the CMV promoter sequence as shown in FIG. 9. As can be readily seen form the FIG. 11, insertion of the operator sequence elements lead to a reduced expression versus control in equal magnitudes. Notably, where the EC7 cells also expressed the lambda repressor, transcription was substantially completely abrogated. Thus, it should be noted that transcription control can be effectively implemented using the lambda operator sequence elements in conjunction with a lambda repressor that includes a nuclear location sequence.

Figure 12:
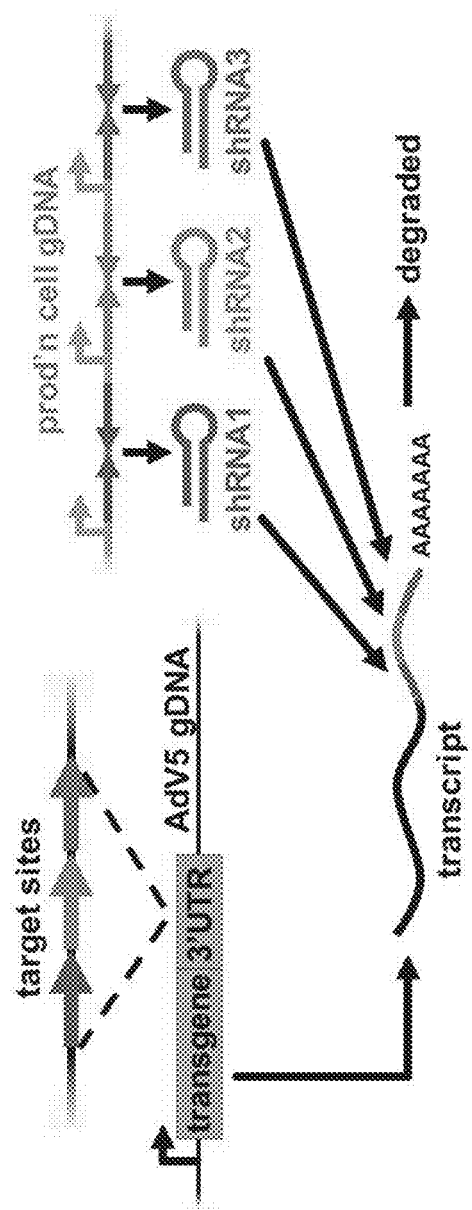
FIG. 12 depicts exemplary genetic modifications of a recombinant virus that binding sequences for shRNA include operator sequences capable of binding the lambda repressor.

In another exemplary approach to suppress transcription, the inventors tested a system as schematically shown in FIG. 12 by generating a genetically modified cell with a construct in the production cell encoding shRNAs designed to bind sequences found in the viral vector or other expression construct. The right portion of FIG. 12 shows genomic DNA with coding regions that give rise to shRNAs as indicated, while the left portion of FIG. 12 depicts a portion of an adenoviral expression system that includes a gene of interest with one or more binding sites for the shRNA in the 3'-UTR. For example, suitable shRNAs can be taken from the luciferase gene, the beta-lactamase gene, and/or the lacZ gene, and the expression system can be viral (e.g., AdV) or plasmid DNA encoding a gene of interest (e.g., GFP) with a 3'UTR containing sequences from luciferase, LacZ, and/or β-lactamase, respectively.

Figure 13:
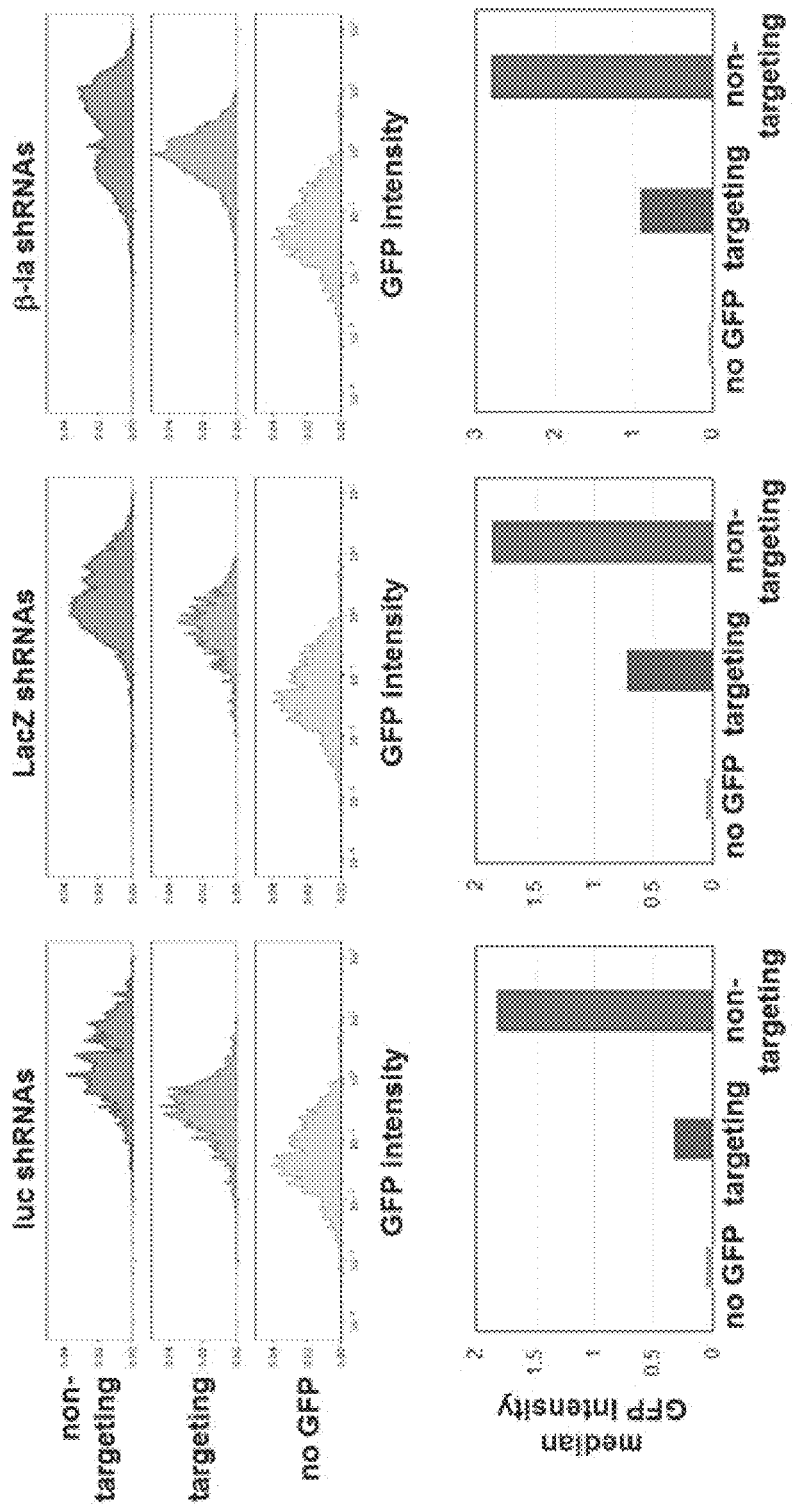
FIG. 13 depicts exemplary results using the expression system of FIG. 12.
Figure 14:
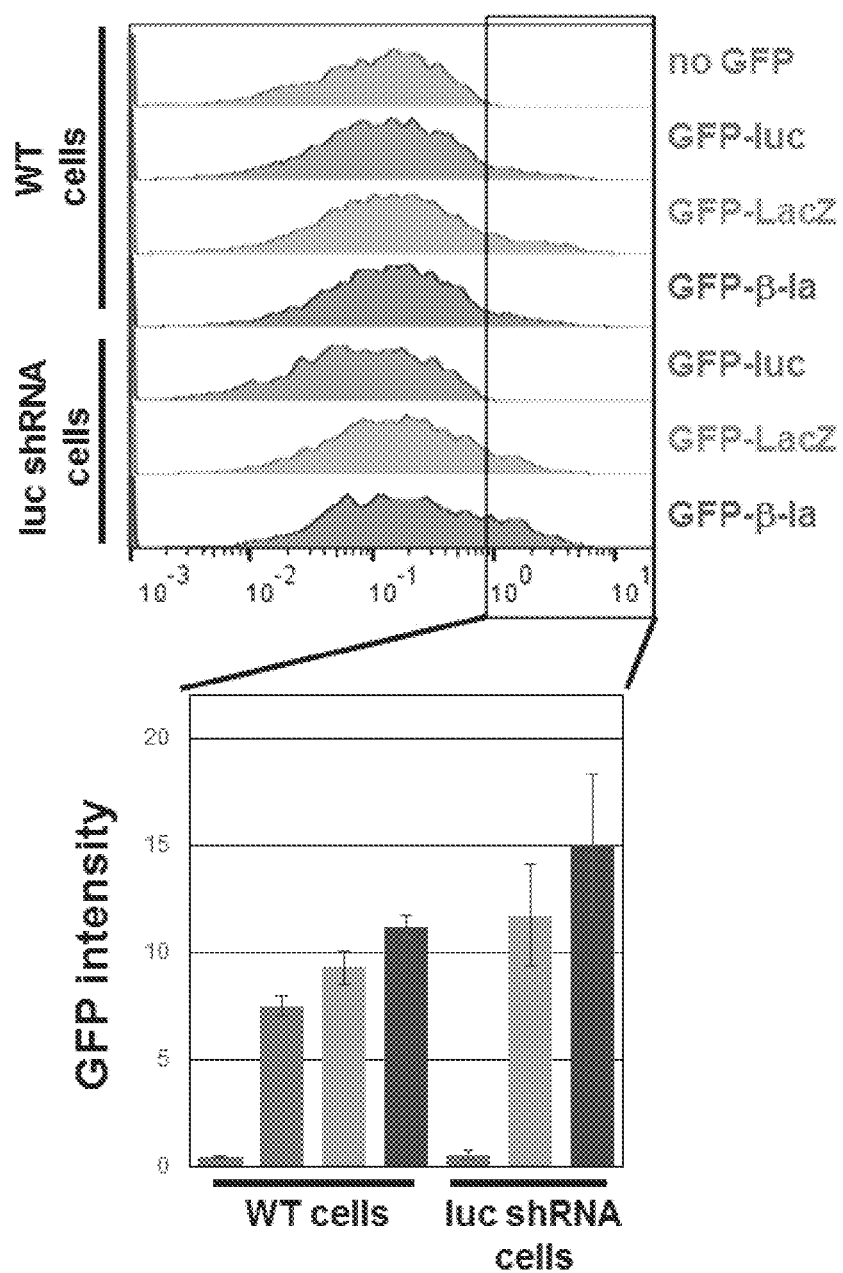
FIG. 14 depicts further exemplary results using the expression system of FIG. 12.

Results for an exemplary test system are shown in FIG. 13. Here the inventors transiently transfected EC7 production cells with a GFP transgene having a 3'UTR containing shRNA target sites taken from one of three different heterologous genes: luciferase, LacZ or β-lactamase. DNA encoding shRNAs that target or do not target (negative controls) these sites were also co-transfected and the GFP intensity in these cells was measured by flow cytometry as a way to access transgene expression. In every case, GFP expression was significantly downregulated when shRNAs targeting its 3'UTR were present compared to non-targeting shRNAs. Likewise, FIG. 14 depicts results from EC7 production cells transfected with a sequence encoding luc shRNA and non-transfected control cells. GFP expression is then monitored for transfections with expression vectors carrying the GFP gene and a shRNA binding site as indicated in the top panel of the figure. As can be readily seen from the results, specific downregulation for GFP was only observed in cells that expressed luc shRNA and that were transfected with constructs that encoded GFP with a luc shRNA binding site. Thus, it should be appreciated that shRNA can effectively downregulate expression of transgenic cargo.

Therefore, the inventors contemplate an exemplary system in which the host cell is genetically modified to transiently, and more preferably permanently, produce one or more shRNA species from a segment of recombinant DNA that may be integrated into the genome or maintained/provided as extrachromosomal unit. Subsequent processing of these species allows them to direct the RNA induced silencing complex (RISC) to degrade transcripts carrying complementary target sequences. As will be appreciated, by housing these complementary target sequences in the 3'UTR of transgenes carried in the AdV5 genome, emerging transcripts are degraded thereby preventing any toxic effects of the would-be gene products. Most preferably, the shRNAs will be selected such that they do not recognize endogenous genes in the production cells. Moreover, it is further contemplated that recombinant constructs/host cells can be generated that express multiple (e.g., at least two, or at least three) different shRNAs along with the 3'UTRs that carry target sites for each of those shRNAs to so enhance the silencing potential.

Figure 15:
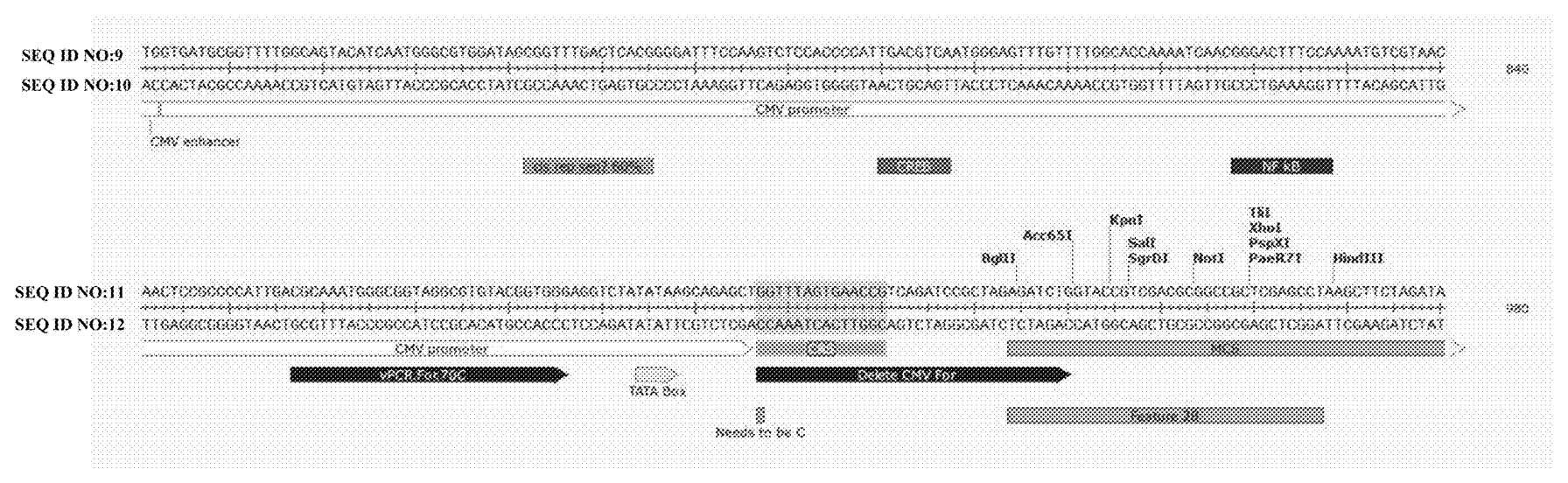
Figure 16:
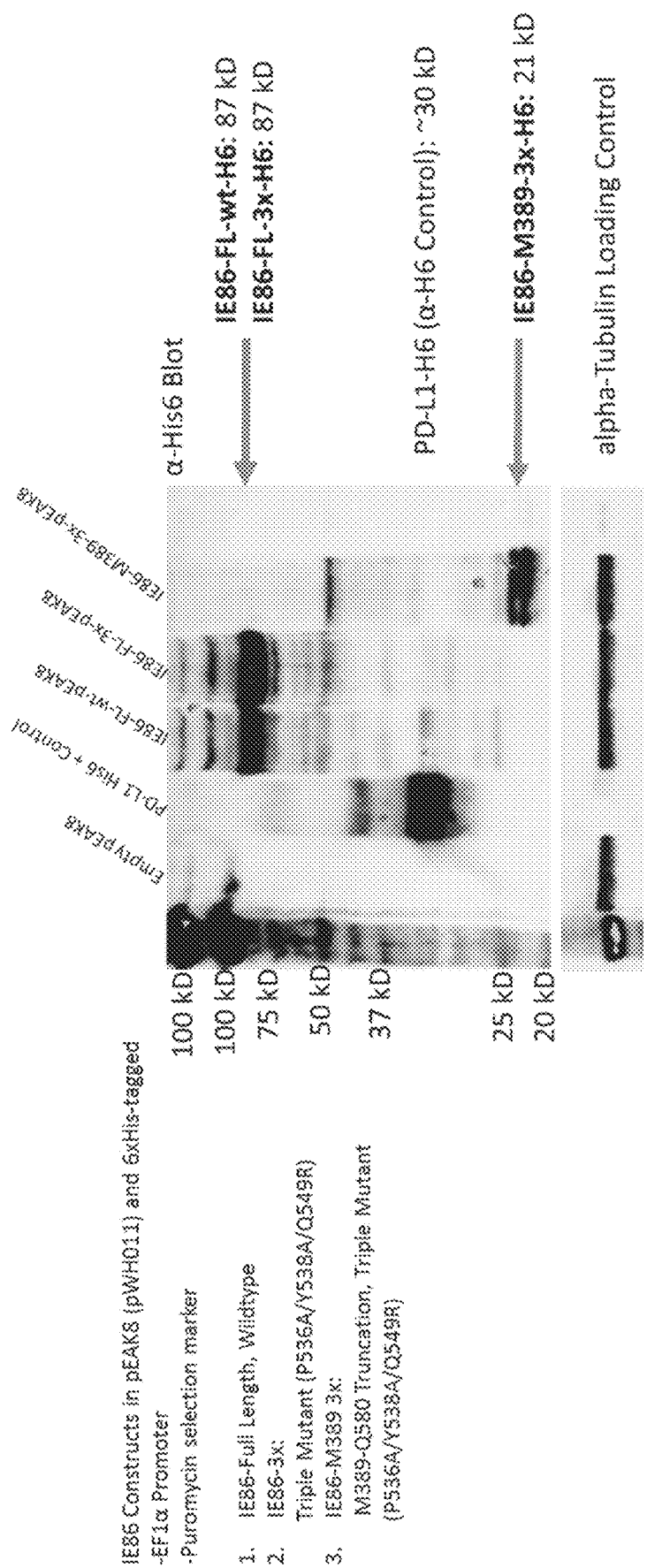
FIG. 16 depicts exemplary results for a gel illustrating expression of IE86 and variants thereof in EC7 host cells used for virus production.
Figure 17:
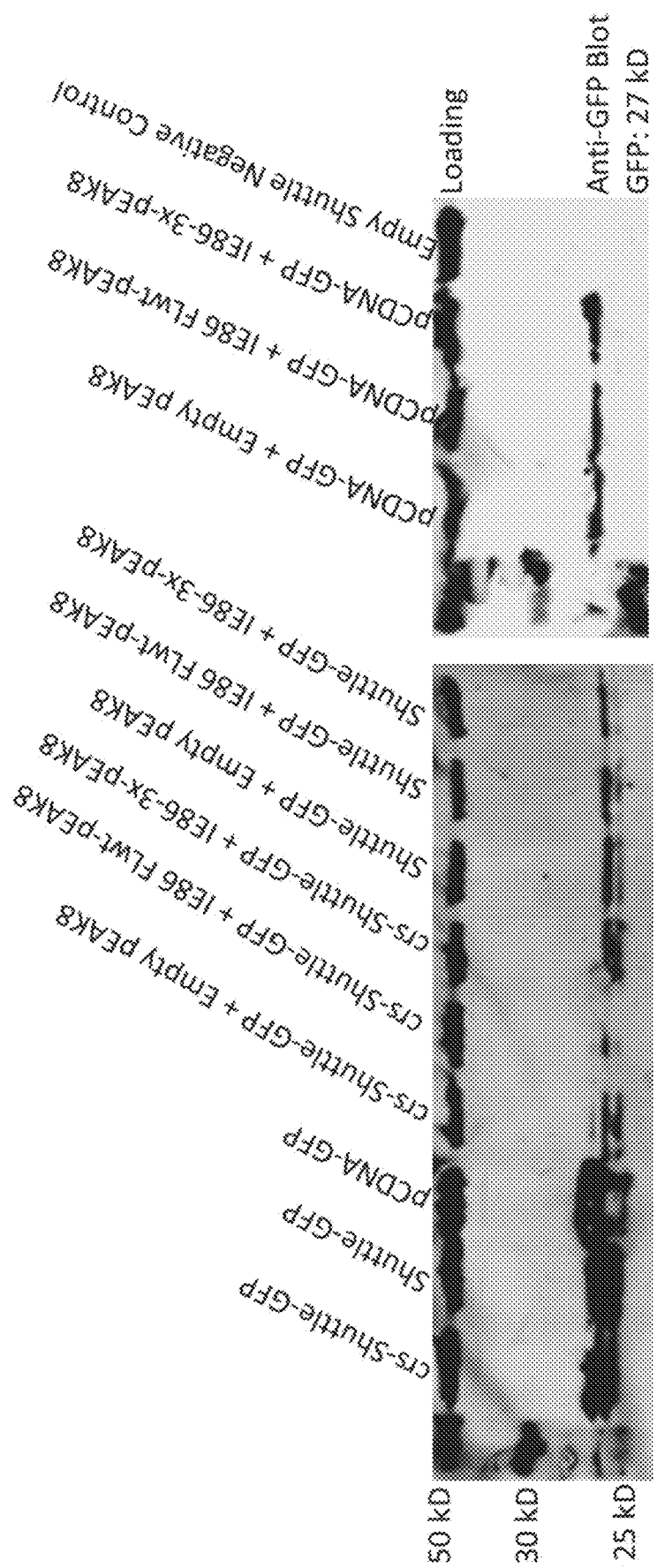
FIG. 17 depicts exemplary results for a gel illustrating expression of GFP from a vector construct that contains an IE86 responsive cis repression sequence (crs) downstream of a promotor using recombinant IE86 and variants thereof in EC7 host cells.
Figure 18:
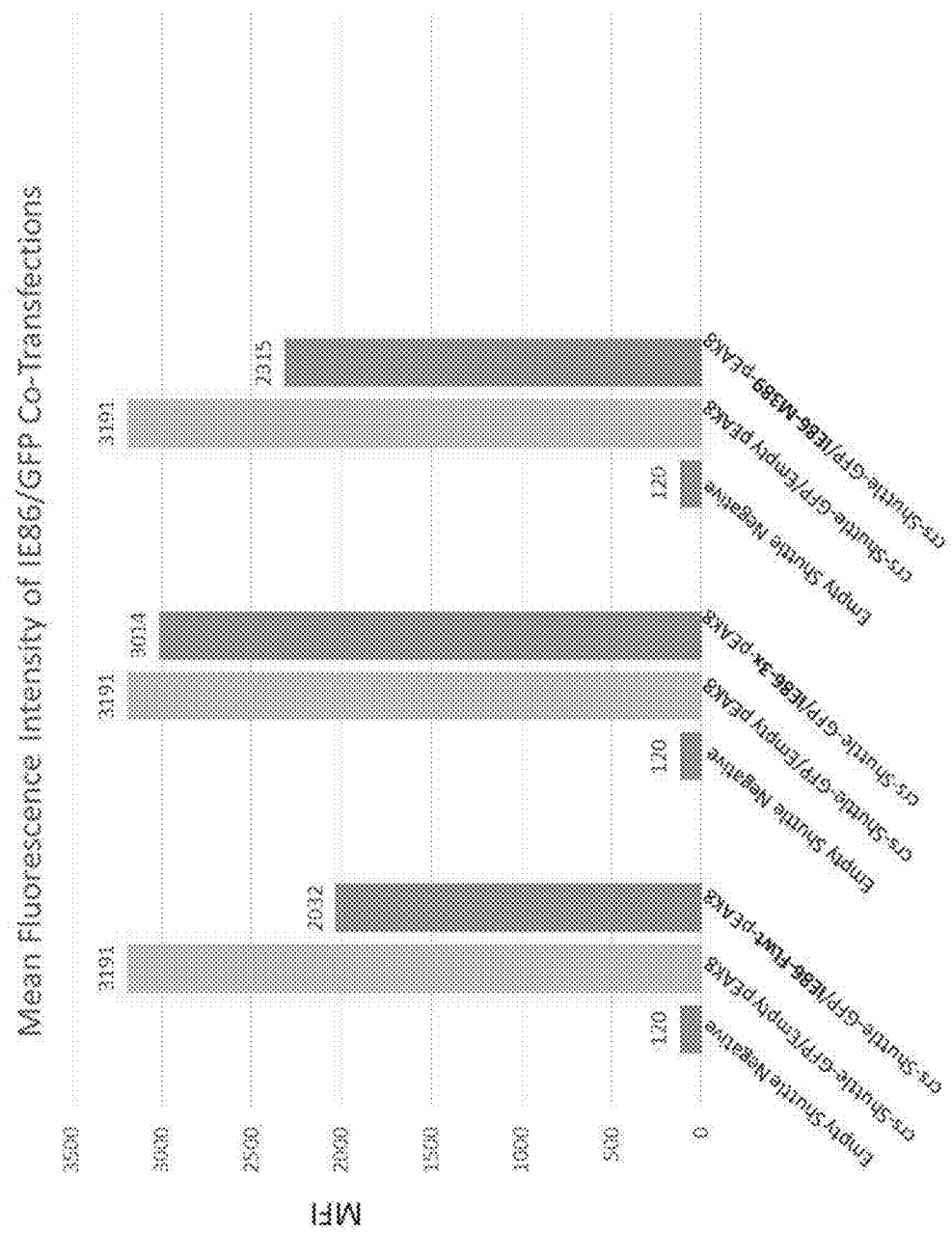
FIG. 18 is a graph depicting exemplary results for suppression of GFP expression using recombinant IE86 and variants thereof in EC7 host cells.

In yet another approach to control transcription, the inventors used a system in which recombinant IE86 (and variants thereof) was expressed in EC7 production cells. Here, IE86 specifically binds to a crs (cis-repression sequence) sequence element, and where the crs sequence element in part of a promotor sequence, transcription can be reduced or suppressed. FIG. 15 depicts an exemplary promotor sequence with a CMV promotor that is followed by a crs sequence element upstream of a multiple-cloning site into which a gene for expression (here: GFP) can be placed. To make recombinant DNA sensitive to suppression by IE86, cells need to recombinantly express IE86. FIG. 16 depicts exemplary results for recombinant expression of IE86 and variants thereof from an expression plasmid (pEAK8) in EC7 cells. As can be readily seen, all recombinant forms expressed well in the production cells. To test functional impact of the so produced IE86 and variant forms, IE86 expressing cells were further transfected with expression constructs that included crs sequence elements in the promotor to control expression of a GFP gene. As can be seen from the results in FIG. 17, the expression constructs that included crs sequence elements in the promotor (crs-shuttle-GFP) downregulated expression of the GFP gene in cells that also expressed IE86. FIG. 18 depicts graphs for the results from flow cytometry for transfected cells as indicated in the graph: NO significant fluorescence was observed for all cells that were not transfected, whereas high fluorescence was measured for cells transfected with expression constructs that included crs sequence elements in the promotor (crs-shuttle-GFP) but not transfected with an expression plasmid that encoded IE86 or variants thereof. Reduced fluorescence was observed with cells transfected with expression constructs that included crs sequence elements in the promotor (crs-shuttle-GFP) and that were transfected with an expression plasmid that encoded IE86 or variants thereof.

ADDITIONAL EXAMPLES

Latent membrane protein 1 (LMP1) is an integral membrane protein of Epstein Barr Virus (EBV), and induce various changes in immune competent cell upon expression in such cells, including activation of dendritic cells and macrophages as a CD40 mimic. Similarly, IPS-1 (interferon-β promoter stimulator 1) activates dendritic cells by inducing type I interferon and interferon-inducible genes. Thus, both LMP-1 and IPS-1 have been suggested as effective co-stimulatory molecules for immunotherapy, more specifically DNA vaccines expressing a tumor associated antigen. Yet, expression of LMP-1 and/or IPS-1 in the host cell during virus replication may affect the virus production level in the host cell.

Example 1

The inventors contemplate that the expression of LMP-1, IPS-1, or a fusion protein LMP-IPS-1 (N-terminal aggregating domain of LMP1 and IPS-1) can be suppressed in the host cell by genetically modifying the host cell to express dominant negative mutant interferon regulatory transcription factor 3 (e.g., IRF3-ΔN, etc.). In this example, the recombinant nucleic acid encoding the payload (LMP-1, IPS-1, LMP-IPS-1, with or without being coupled with tumor associated antigens) also includes a promoter responsive to IRF3 (e.g., IFN-α promoter, IFN-β promoter, etc.) that is operationally coupled to the payload genes. It is contemplated that dominant negative mutant IRF3 inhibit transcription of payload genes such that the expression of the payload proteins can be reduced or eliminated in the host cell.

Example 2

The inventors contemplate that the expression of LMP-1, IPS-1, or a fusion protein LMP-IPS-1 can be suppressed in the host cell by genetically modifying the host cell to express regulatory/inhibitory RNA (e.g., shRNA, siRNA, miRNA, etc.) specific to LMP-1, IPS-1, or 5'- or 3'-UTR flanking those coding sequences. It is contemplated that the regulatory/inhibitory RNA can destabilize the transcripts of payload genes and/or inhibit their translation such that the expression of the payload genes can be substantially reduced or eliminated in the host cell. In some embodiments, the host cell can be genetically modified to constitutively express regulatory/inhibitory RNA. In other embodiments, the host cell can be genetically modified to conditionally produce regulatory/inhibitory RNA. For example, the payload may also include a nucleic acid fragment encoding ecdysone (an insect steroid hormone) in an open reading frame under the same promoter with the other payload genes (LMP-1, IPS-1, or LMP-IPS-1). The host cell can be genetically modified to express regulatory/inhibitory RNA under an ecdysone responsive promoter. In such example, the regulatory/inhibitory RNA includes those specific to LMP-1, IPS-1, or LMP-IPS-1, and at least one specific to ecdysone such that the payload is expressed only when the payload genes began to be transcribed. Thus, the expression of regulatory/inhibitory RNA is conditional to the expression of payload proteins and the regulatory/inhibitory RNA may not be unnecessarily expressed in the host cell absence of expression of payload.

Example 3

The inventors contemplate that the expression of IPS-1 or a fusion protein LMP-IPS-1 can be suppressed in the host cell by genetically modifying the host cell to express a binding molecule that inactivates or breaks down the payloads such that any toxicity originating from the payloads to the host cell can be reduced or eliminated and/or any functions of the payloads can be attenuated. For example, the host cell can express hepatitis C NS3-4a protease, which specifically cleaves IPS-1. In some embodiments, the host cell can be genetically modified to constitutively hepatitis C NS3-4a protease. In other embodiments, the host cell can be genetically modified to conditionally produce hepatitis C NS3-4a protease. For example, the host cell can be genetically modified to express hepatitis C NS3-4a protease under IRF3 promoter that responds to the transcription factors downstream of IPS-1 signaling. In such example, hepatitis C NS3-4a protease is expressed only when the payload genes began to be transcribed and expressed to so initiate the IPS-1 signaling pathway. Thus, the expression of hepatitis C NS3-4a protease is conditional to the expression of payload proteins and the hepatitis C NS3-4a protease may not be unnecessarily expressed in the host cell absence of expression of payload.

Example 4

The inventors contemplate that the expression of IPS-1 or a fusion protein LMP-IPS-1 can be suppressed in the host cell by genetically modifying the host cell to express a one or more shRNA molecules that will bind to the mRNA transcript of the IPS-1 or fusion protein to so lead to degradation of the mRNA. To that end, the inventors generated a test system in which transgenic cargo expression is suppressed by short hairpin RNAs (shRNAs) that are stably generated by the production cells (e.g., EC7 cells, CHO cells, etc) allowing for unhindered viral amplification.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of producing two preparations of recombinant therapeutic adenoviruses, the method comprising:
   providing EC7 cells, wherein each of the EC7 cells express from a recombinant nucleic acid, a chimeric protein comprising a lambda repressor portion and a nuclear location sequence (NLS), wherein the NLS sequence is downstream of the lambda repressor;
   providing a first plurality of recombinant adenoviruses comprising a genome with a first recombinant sequence portion that encodes a first cargo sequence and an operator sequence and a promotor sequence operably linked to the cargo sequence;
   producing a first preparation of recombinant therapeutic adenovirus by (a) transfecting a first plurality of the EC7 cells with the genomes of the first plurality of recombinant adenoviruses, and (b) culturing the first plurality of transfected EC7 cells until they produce a first viral titer of at least $10^9$ viral particles/mL;
   providing a second plurality of recombinant adenoviruses comprising a genome with a second recombinant sequence portion that encodes a second cargo sequence and an operator sequence, and a promotor sequence operably linked to the cargo sequence:
   producing a second preparation of recombinant therapeutic adenovirus by (a) transfecting a second plurality of the EC7 cells with the genomes of the second plurality of recombinant adenovirus, and (b) culturing the second plurality of transfected EC7 cells until they produce a second viral titer of at least $10^9$ viral particles/mL;
   wherein there is 20% variation or less between the time necessary to culture the first preparation to a titer of at least $10^9$ viral particles/mL and the time necessary to culture the second preparation to a titer of at least $10^9$ viral particles/mL.

2. The method of claim 1, wherein the first and the second plurality of EC7 cells further expresses CXADR from a recombinant nucleic acid.

3. The method of claim 1, wherein the first plurality and/or the second plurality of recombinant adenovirus are E2b-deleted adenovirus.

4. The method of claim 1, wherein the first plurality and/or the second plurality of recombinant adenovirus genomes further comprises a viral payload gene that encodes at least one of a cytokine, a chimeric protein, a tumor associated antigen, and a neoepitope.

5. The method of claim 1, wherein the first and the second viral titer is at least $10^{10}$ viral particles/mL.

6. The method of claim 1, wherein the first and the second viral titer is reached within a time period having a variability of equal or less than 10% between the first and the second EC7 cells.

7. The method of claim 1, wherein the first cargo sequence and the second cargo sequence are the same.

8. The method of claim 1, wherein the first cargo sequence and the second cargo sequence are different.

* * * * *